US011225639B2

(12) United States Patent
Sakuma et al.

(10) Patent No.: US 11,225,639 B2
(45) Date of Patent: Jan. 18, 2022

(54) CELL SORTING DEVICE (71) Applicant: National University Corporation Nagoya University, Nagoya (JP)

(72) Inventors: Shinya Sakuma, Nagoya (JP); Takeshi Hayakawa, Nagoya (JP); Fumihito Arai, Nagoya (JP)

(73) Assignee: NATIONAL UNIVERSITY CORPORATION NAGOYA UNIVERSITY, Aichi (JP)

( * ) Notice: Subject to any disclaimer, the term of this patent is extended or adjusted under 35 U.S.C. 154(b) by 540 days.

(21) Appl. No.: 16/085,412

(22) PCT Filed: Mar. 6, 2017

(86) PCT No.: PCT/JP2017/008722
§ 371 (c)(1),
(2) Date: Nov. 8, 2018

(87) PCT Pub. No.: WO2017/159422
PCT Pub. Date: Sep. 21, 2017

(65) Prior Publication Data
US 2019/0071630 A1 Mar. 7, 2019

(30) Foreign Application Priority Data
Mar. 17, 2016 (JP) .............................. JP2016-053233

(51) Int. Cl.
*C12M 1/00* (2006.01)
(52) U.S. Cl.
CPC .................... *C12M 47/04* (2013.01)
(58) Field of Classification Search
CPC ...... C12M 23/16; C12M 23/34; C12M 47/04; G01N 15/1404; G01N 15/1427;
(Continued)

(56) References Cited

U.S. PATENT DOCUMENTS

2010/0104474 A1* 4/2010 Van Haag ................. F15C 5/00
422/68.1
2011/0081674 A1* 4/2011 Han ....................... C12Q 1/025
435/29

(Continued)

FOREIGN PATENT DOCUMENTS

JP 2004-93558 A 3/2004
JP 2008111798 A 5/2008
(Continued)

*Primary Examiner* — Benjamin R Whatley
*Assistant Examiner* — Austin Q Le
(74) *Attorney, Agent, or Firm* — Fox Rothschild LLP; Robert J. Sacco; Carol E. Thorstad-Forsyth (57) ABSTRACT

A cell sorting device is characterized by including: a main flow channel (14) through which a liquid containing a row of cells including a target cell flows, and in which a cell separation area for separating the target cell from the row of cells is provided at a halfway position in a flow direction, the main flow channel being formed in a substrate (12); a selection flow channel (16) into which the target cell is pushed out from the main flow channel, the selection flow channel being formed in the substrate so as to branch from the main flow channel downstream of the cell separation area; a sub flow channel (18) through which a separating liquid flows, the separating liquid being for separating the target cell from the row of cells and pushing out the target cell into the selection flow channel, the sub flow channel being formed in the substrate so as to intersect with the main flow channel in the cell separation area; a pair of liquid flow generating members (22) for generating a liquid flow of the separating liquid in the sub flow channel, the liquid flow generating members being provided at one end and the other end of the sub flow channel; and a drive control member (23) for actuating the pair of liquid flow generating members, wherein the drive control member actuates the pair of liquid flow generating members in conjunction with each other so (Continued)

that the separating liquid forms a liquid flow in a first direction from the one end to the other end of the sub flow channel and a liquid flow in a second direction opposite to the first direction.

9 Claims, 6 Drawing Sheets

(58) Field of Classification Search
CPC ........... G01N 15/1459; G01N 15/1484; G01N 21/53; G01N 21/6486; G01N 2015/149; G01N 2015/1409
See application file for complete search history.

(56) References Cited

U.S. PATENT DOCUMENTS

| | | | |
|---|---|---|---|
| 2011/0294139 A1* | 12/2011 | Takeda | G01N 15/1484 435/7.1 |
| 2012/0034677 A1* | 2/2012 | Delamarche | C12M 23/16 435/235.1 |

FOREIGN PATENT DOCUMENTS

| | | | |
|---|---|---|---|
| JP | 2008122396 A | 5/2008 | |
| JP | 2009174995 A | 8/2009 | |
| WO | 2016006642 A1 | 1/2016 | |

* cited by examiner

CELL SORTING DEVICE

CROSS REFERENCE TO RELATED APPLICATION

The present application is the U.S. national Stage of PCT International Patent Application No. PCT/JP2017/008722 filed on Mar. 6, 2017, which claims priority to Japanese Patent Application No. 2016-053233 filed on Mar. 17, 2016. All of the aforementioned applications are incorporated herein by reference in their entireties.

TECHNICAL FIELD

The present invention relates to a cell sorting device.

BACKGROUND ART

Unlike other materials, cellular materials have large individual differences from cell to cell, so it is increasingly important to understand such individual differences to operate and sort individual cells in cell biology and cell engineering.

There has been known a technique which, using a microchip having a substrate such as glass provided with micro flow channels, flows a liquid containing a target cell through a micro flow channel, and changes flow channels and sorts out the cell according to the characteristics of the cell. For example, Patent Literature 1 describes a particle sorting system provided with a side passage communicating with a measurement conduit and with a branch conduit. In Patent Literature 1, the actuator provided in the side passage is operated to deflect a liquid flow, and a selected target particle (cell) is flown into the branch conduit and sorted.

CITATION LIST

Patent Literature

Patent Literature 1: Japanese Patent Laid-Open No. 2008-122396

SUMMARY OF INVENTION

Technical Problem

It is required to raise the ratio of target cells among sorted-out cells (success rate of sorting) and to sort out target cells at a higher speed.

Accordingly, an object of the present invention is to provide a cell sorting device capable of sorting out target cells at a higher success rate and at a higher speed.

Solution to Problem

A cell sorting device according to the present invention includes: a substrate; a main flow channel through which a liquid containing a row of cells including a target cell flows, and in which a cell separation area for separating the target cell from the row of cells is provided at a halfway position in a flow direction, the main flow channel being formed in the substrate; a selection flow channel into which the target cell is pushed out from the main flow channel, the selection flow channel being formed in the substrate so as to branch from the main flow channel downstream of the cell separation area; a sub flow channel through which a separating liquid flows, the separating liquid being for separating the target cell from the row of cells and pushing out the target cell into the selection flow channel, the sub flow channel being formed in the substrate so as to intersect with the main flow channel in the cell separation area; a pair of liquid flow generating members for generating a liquid flow of the separating liquid in the sub flow channel, the pair of liquid flow generating members being provided at one end and the other end of the sub flow channel; and a drive control member for actuating the pair of liquid flow generating members, wherein the drive control member actuates the pair of liquid flow generating members in conjunction with each other so that the separating liquid forms a liquid flow in a first direction from the one end to the other end of the sub flow channel and a liquid flow in a second direction opposite to the first direction.

Advantageous Effects of Invention

According to the present invention, a cell sorting device has a sub flow channel which intersects with a main flow channel through which a liquid containing target cells flows, and a separating liquid flows through the sub flow channel. The separating liquid can flow in both directions in the sub flow channel, so that the target cells can be efficiently separated.

A liquid flow of the separating liquid in the sub flow channel is generated by a pair of liquid flow generating members provided on opposite ends of the sub flow channel. The pair of liquid flow generating members operate in conjunction with each other, so that the target cells can be separated at a higher speed. When separating the target cells, the liquid flow of the separating liquid is prevented from excessively disturbing the flow of the liquid flowing through the main flow channel.

As described above, since the pair of liquid flow generating members operating in conjunction with each other are provided on both ends of the sub flow channel which intersects with the main flow channel and the liquid flow of the separating liquid is generated in both directions, target cells can be sorted out at a higher success rate and at a higher speed.

BRIEF DESCRIPTION OF DRAWINGS

FIG. 7 is a schematic diagram illustrating a liquid flow of a separating liquid inside a sub flow channel, in which

DESCRIPTION OF EMBODIMENTS

Hereinafter, embodiments of the present invention will be described in detail with reference to the drawings.

(Overall Configuration)

Figure 1:
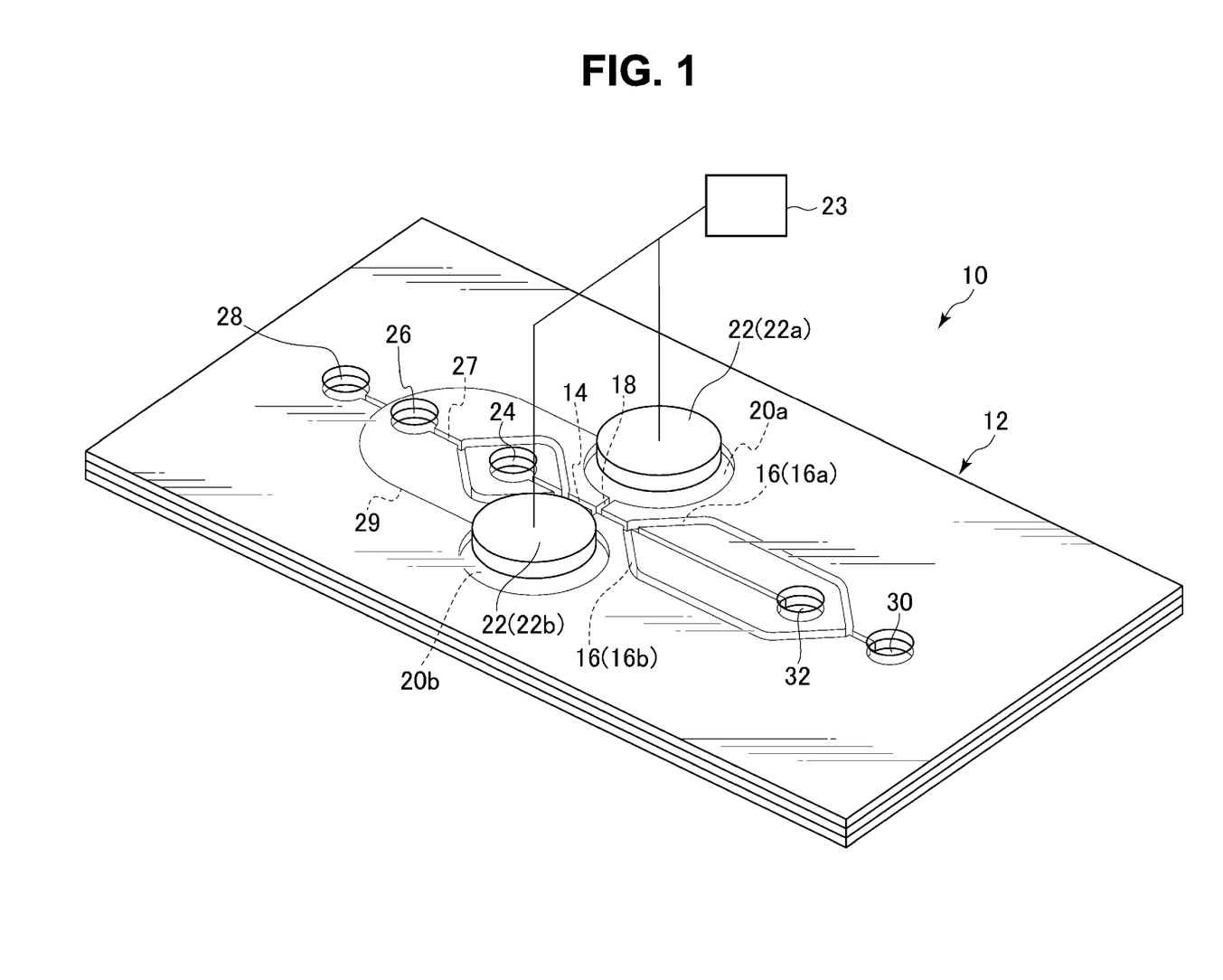
FIG. 1 is a perspective view illustrating a configuration of a cell sorting device according to an embodiment.
Figure 2:
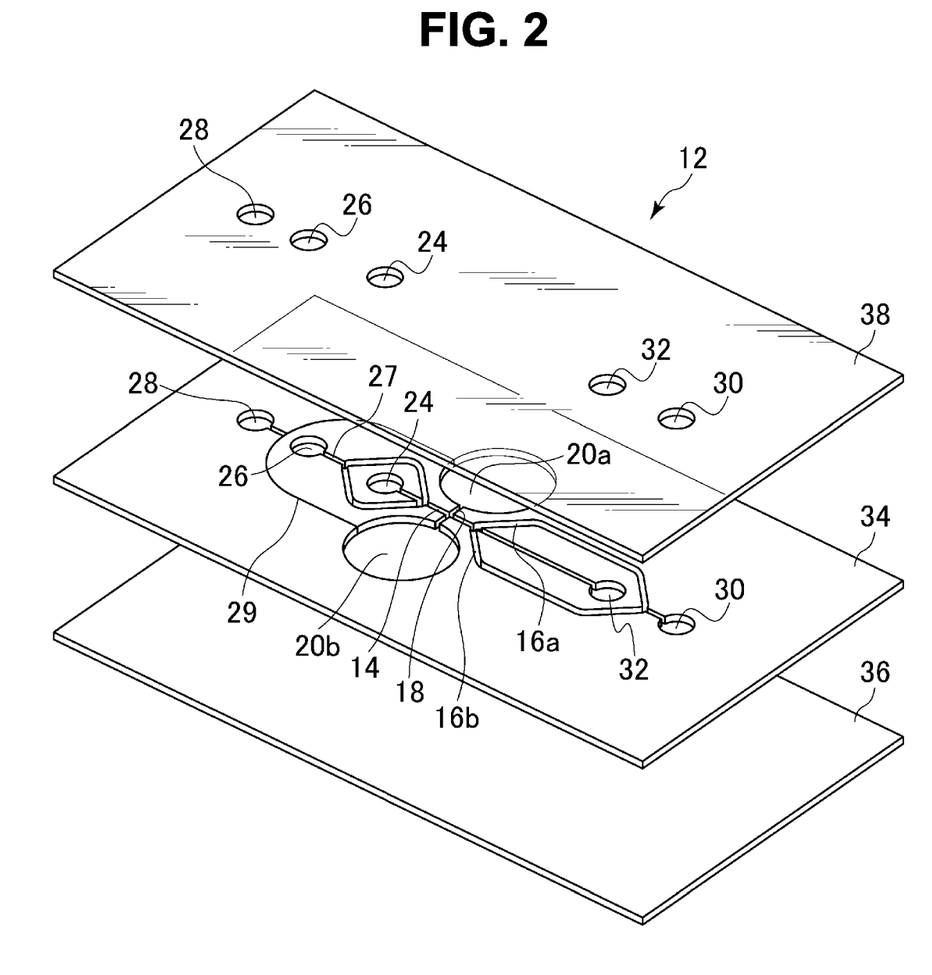
FIG. 2 is an exploded perspective view illustrating a configuration of a substrate in the cell sorting device according to the embodiment.

A cell sorting device 10 shown in FIG. 1 includes a substrate 12 with flow channels formed therein, a pair of liquid flow generating members 22 arranged on the substrate 12, and a drive control member 23 connected to the pair of liquid flow generating members 22. As shown in FIG. 2, the substrate 12 includes a flow channel layer 34, a support layer 36 provided on the lower surface of the flow channel layer 34, and a deformable covering layer 38 covering the upper surface of the flow channel layer 34. The thickness of the substrate 12 may be, for example, about 0.3 to 2 mm.

In this embodiment, the flow channel layer 34 is made of silicon. In the flow channel layer 34, the main flow channel 14 is formed through which a liquid containing a row of cells including a target cell (now shown) flows. The width of the main flow channel 14 can be appropriately set according to the size of a cell contained in the liquid. For example, in a case where the cell size is about 50 to 100 μm, the width of the main flow channel 14 may be about 50 to 500 μm. In this case, a liquid containing a row of cells including a target cell can flow through the main flow channel 14 at a flow rate of about 0.01 to 10 m/sec. The flow rate of a liquid flowing through the main flow channel 14 may be controlled by, for example, a syringe pump, a rotary pump, a centrifugal pump, a pneumatic pump, or the like (not shown).

The main flow channel 14 has a sample inlet 24 into which a liquid containing a target cell is injected, at the upstream end. At the downstream end of the main flow channel 14, a waste port 32 for collecting non-target cells is provided. In this embodiment, the sample inlet 24 and the waste port 32 are substantially circular openings with a diameter of about 1.5 mm. Further, the main flow channel 14 has a cell separation area (not shown) for separating a target cell from a row of cells, in a halfway position in the flow direction.

In the flow channel layer 34, a sub flow channel 18 is formed so as to intersect with the main flow channel 14 in the cell separation area. A separating liquid (hereinafter also referred to as a buffer solution) for separating a target cell from a row of cells flows through the sub flow channel 18.

A first liquid reservoir 20a and a second liquid reservoir 20b are provided at one end and the other end of the sub flow channel 18, respectively. In this embodiment, as described later, a pair of liquid flow generating members 22 are arranged above the first and second liquid reservoirs 20a, 20b. It is desirable that the size and shape of the first and second liquid reservoirs 20a, 20b are appropriately set according to the size and shape of the pair of liquid flow generating members 22 so that the actions of the liquid flow generating members are sufficiently transmitted.

The distance between the first liquid reservoir 20a and the second liquid reservoir 20b is preferably as short as possible. For example, in a case where the width of the main flow channel 14 is about 100 to 200 μm and the width of the sub flow channel 18 is about 50 to 200 μm, the distance between the first liquid reservoir 20a and the second liquid reservoir 20b may be about 0.1 to 10 mm.

In the downstream of the cell separation area, a selection flow channel 16 branches from the main flow channel 14. A target cell separated from the row of cells in the cell separation area is pushed out into the selection flow channel 16. The width of selection flow channel 16 can be appropriately selected according to the size of the target cell. The distance from the cell separation area to the selection flow channel 16 may also be appropriately selected according to the size of the target cell or the like. In this embodiment, the selection flow channel 16 includes two branch flow channels (a first branch channel 16a and a second branch channel 16b). The first and second branch channels 16a, 16b are provided symmetrically with respect to the main flow channel 14 on opposite sides thereof, and join downstream.

At the downstream end of the selection flow channel 16 where the first and second branch flow channels 16a, 16b join, a sorting port 30 for collecting target cells is provided. In this embodiment, the sorting port 30 is a substantially circular opening with a diameter of about 1.5 mm.

The flow channel layer 34 is further provided with a sheath liquid inlet 26, a sheath liquid flow channel 27, a buffer solution inlet 28, and a buffer solution flow channel 29. In this embodiment, the sheath liquid inlet 26 and the buffer solution inlet 28 are substantially circular openings with a diameter of about 1.5 mm. A sheath liquid is supplied via the sheath liquid flow channel 27 to the main flow channel 14, to carry cells by wrapping them. As the sheath liquid is supplied, the cells in the liquid are aligned along the flow direction to form a row of cells. A buffer solution is supplied via the buffer solution flow channel 29 to the first and second liquid reservoirs 20a, 20b on opposite ends of the sub flow channel 18. The buffer solution flows through the sub flow channel 18 between the first liquid reservoir 20a and the second liquid reservoir 20b, as a separating liquid for separating target cells.

As the sheath liquid and the buffer solution, a liquid similar to the liquid flowing through the main flow channel 14 may be used. A liquid different from the liquid flowing through the main flow channel 14 may be used as the sheath liquid and the buffer solution if it does not adversely affect target cells.

The thickness of the flow channel layer 34 is not particularly limited as long as the above described flow channels (the main flow channel 14, the sub flow channel 18, the selection flow channel 16), inlets (the sample inlet 24, the sheath liquid inlet 26, the buffer solution inlet 28), and ports (the sorting port 30, the waste port 32) can be formed. The thickness of the flow channel layer 34 may be, for example, about 0.1 to 0.5 mm.

Preferably, the covering layer 38 is elastically deformable. In this embodiment, the covering layer 38 is made of borosilicate glass. The covering layer 38 is provided with the sample inlet 24, the sheath liquid inlet 26, the buffer solution inlet 28, the sorting port 30, and the waste port 32 so as to match with the flow channel layer 34 when stacked thereon. Thereby, through the covering layer 38 of the substrate 12, samples, sheath liquid, and buffer solution can be injected into their respective inlets (the sample inlet 24, the sheath liquid inlet 26, and the buffer solution inlet 28). Target cells collected in the sorting port 30 can be picked up through the covering layer 38.

The covering layer 38 is preferably as thin as possible to the extent that strength and elasticity can be maintained. The thickness of the covering layer 38 may be, for example, about 0.1 to 1 mm.

The support layer 36 is a plate-like member having a flat surface, and is not particularly processed. In this embodiment, the support layer 36 is made of borosilicate glass. The support layer 36 may be formed with any thickness as long as the flow channel layer 34 and the covering layer 38 can be supported.

The pair of liquid flow generating members 22 includes a first liquid flow generating member 22a provided on the substrate 12 surface above the first liquid reservoir 20a, and a second liquid flow generating member 22b provided on the substrate 12 surface above the second liquid reservoir 20b. The pair of liquid flow generating members 22 operate in conjunction with each other by a drive signal from the drive control member 23 (see FIG. 1). Thereby, a liquid flow in the first direction from the first liquid reservoir 20a to the second liquid reservoir 20b and a liquid flow in the second direction from the second liquid reservoir 20b to the first liquid reservoir 20a are generated inside the sub flow channel 18.

In this embodiment, piezoelectric elements are used as the first liquid flow generating member 22a and the second liquid flow generating member 22b. Specifically, a piezoelectric actuator (model number: PAC166J) manufactured by Nihon Ceratec Co., Ltd. is used as a piezoelectric element. The first liquid flow generating member 22a and the second liquid flow generating member 22b are supplied with a drive signal from a respective high-voltage power supply (not shown). As the high-voltage power supply, a power supply (model number: HAS-4014) manufactured by NF Corporation Co., Ltd. is used.

Control signals are sent from the drive control member 23 to the pair of high-voltage power supplies. In this embodiment, as the drive control member 23, a function generator (model number: WF1968) manufactured by NF Corporation Co., Ltd. is used.

(Operation and Effect)

Figure 3:
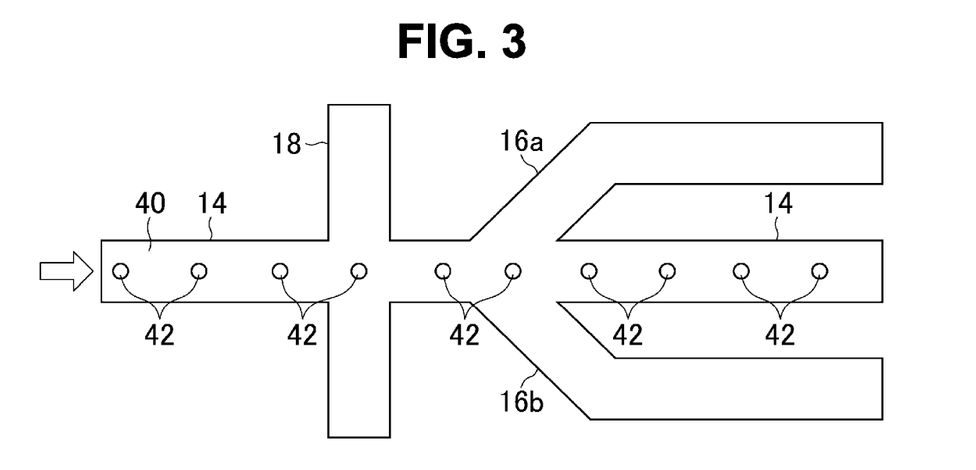
FIG. 3 is a schematic diagram illustrating the flow of a non-target cell in the cell sorting device.

In the cell sorting device 10 configured as described above, a liquid containing a row of cells including a target cell flows through the main flow channel 14. The row of cells includes a non-target cell as well as a target cell. As shown in FIG. 3, non-target cells 42 among cells included in a row of cells in a liquid 40 are carried downstream in the main flow channel 14, and collected in the waste port 32 (see FIG. 1).

Figure 4:
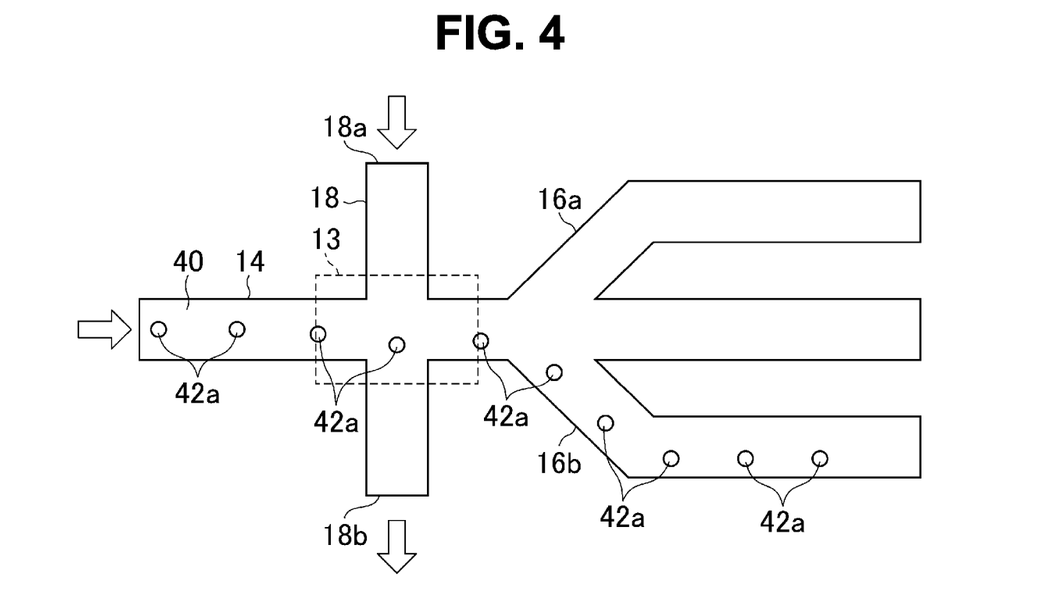
FIG. 4 is a schematic diagram illustrating an example of the flow of a target cell in the cell sorting device.

If a target cell 42a is recognized in the row of cells contained in the liquid 40, a liquid flow of a separating liquid (not shown) is generated, for example, in the first direction from one end 18a side to the other end 18b side of the sub flow channel 18 as shown in FIG. 4.

As shown in FIG. 1, the first and second liquid flow generating members 22a, 22b are provided at the one end and the other end of the sub flow channel 18, respectively. When a target cell 42a is recognized in the row of cells, the first liquid flow generating member 22a on the one end 18a side receives a signal from the drive control member 23, and then operates to push a part of the separating liquid in the first liquid reservoir 20a toward the second liquid reservoir 20b. In conjunction with this, the second liquid flow generating member 22b on the other end 18b side operates to pull the part of the separating liquid in the first liquid reservoir 20a toward the second liquid reservoir 20b. Thus, the part of the separating liquid in the first liquid reservoir 20a is pushed into the sub flow channel 18 and further pulled toward the second liquid reservoir 20b.

In this way, a liquid flow of the separating liquid from the one end 18a side toward the other end 18b side of the sub flow channel 18 is generated, and crosses the liquid 40 flowing through the main flow channel 14. As a result, the target cell 42a deviates from the row of cells in a cell separation area 13 where the main flow channel 14 intersects with the sub flow channel 18, and pushed out into the second branch channel 16b. The target cell 42a pushed out into the second branch channel 16b is collected in the sorting port 30 (see FIG. 1).

Figure 5:
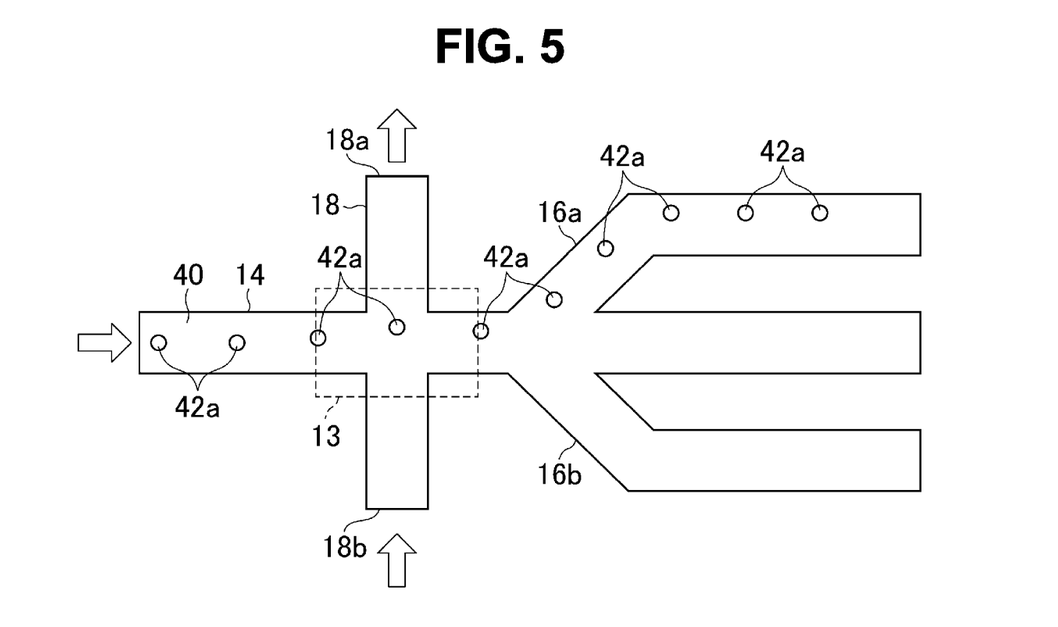
FIG. 5 is a schematic diagram illustrating another example of the flow of a target cell in the cell sorting device.

Alternatively, a liquid flow of the separating liquid (not shown) from the other end 18b toward the one end 18a of the sub flow channel 18 is generated in the second direction opposite to the first direction as shown in FIG. 5. In this case, the second liquid flow generating member 22b on the other end 18b side receives a signal from the drive control member 23, and then operates to push a part of the separating liquid in the second liquid reservoir 20b toward the first liquid reservoir 20a. In conjunction with this, the first liquid flow generating member 22a on the one end 18a side operates to pull the part of the separating liquid in the second liquid reservoir 20b toward the first liquid reservoir 20a. Thus, the part of the separating liquid in the second liquid reservoir 20b is pushed into the sub flow channel 18 and further pulled toward the first liquid reservoir 20a.

In this way, a liquid flow of the separating liquid from the other end 18b side toward the one end 18a side of the sub flow channel 18 is generated, and crosses the liquid 40 flowing through the main flow channel 14. As a result, the target cell 42a deviates from the row of cells in a cell separation area 13, and pushed out into the first branch channel 16a. The target cell 42a pushed out into the first branch channel 16a is also collected in the sorting port 30 (see FIG. 1).

Figure 6:
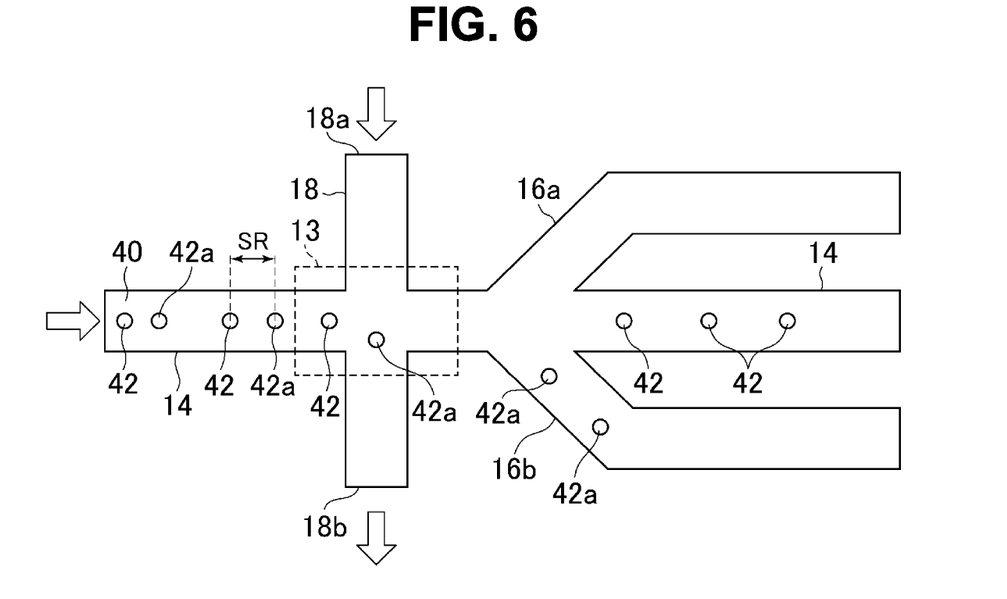
FIG. 6 is a schematic diagram illustrating a spatial resolution (SR)

In the cell sorting device 10, it is ideal that all of the plurality of cells collected in the sorting port 30 are target cells 42a, while non-target cells 42 are collected in the waste port 32. The higher the probability of separating a target cell 42a from the row of cells, the ratio of target cells 42a among a plurality of sorted-out cells can be increased. For separating a non-target cell 42 and a target cell 42a that are adjacent, a predetermined interval is required between these two cells. The shortest interval at which a non-target cell 42 and a target cell 42a can be separated is illustrated in FIG. 6 as the spatial resolution SR. As the interval for the spatial resolution SR is shorter, target cells 42a can be separated in a state where a plurality of cells are arranged more closely. Accordingly, the sorting throughput of target cells 42a is improved.

As described above, the liquid flow of the separating liquid inside the sub flow channel 18 is generated by performing pushing and pulling of the separating liquid in conjunction with each other in the first and second liquid reservoirs 20a, 20b at opposite ends of the sub flow channel 18. Since pushing as well as pulling of the separating liquid are performed in the sub flow channel 18, when the liquid flow of the separating liquid crosses the main flow channel 14, the extent to which pressure propagates to the liquid 40 flowing through the main flow channel 14 is restricted. An area where the flow of the liquid 40 flowing through the main flow channel 14 is influenced by the liquid flow of the separating liquid is the intersection of the main flow channel 14 and the sub flow channel 18, and the vicinity thereof.

Since such a liquid flow of the separating liquid is used, target cells 42a can be separated from a row of cells without interfering with other cells on the upstream side and the downstream side of the cell separation area 13. As a result, the shortest interval at which a target cell 42a can be separated from a non-target cell 42 becomes shorter, which leads to improvement of the spatial resolution SR.

By controlling the pair of liquid flow generating members 22, the amount of the separating liquid pushed into the sub flow channel 18 can be made equal to the amount of the separating liquid pulled from the sub flow channel 18. In this case, the amount of the separating liquid that flows into the cell separation area 13 equals to the amount of the separating liquid that flows out of the cell separation area 13. Thereby, an area where the flow of the liquid flowing through the main flow channel 14 is influenced can be substantially restricted to only an area where the main flow channel 14 intersects with the sub flow channel 18.

Further, liquid flows in two directions, i.e., the first direction from the one end 18a to the other end 18b and the second direction from the other end 18b to one end 18a can be generated inside the sub flow channel 18 intersecting with the main flow channel 14. When a target cell 42a is recognized, a liquid flow of the separating liquid crosses the main flow channel 14 in either one direction, and accordingly the target cell 42a in the row of cells is led to either of the two branch channels 16a, 16b. When no target cell 42a is recognized, any liquid flow of the separating liquid does not cross the main flow channel 14, and therefore a non-target cell 42 in the row of cells is carried downstream in the main flow channel 14.

For example, in a case where two or more target cells 42a are recognized consecutively in the row of cells, every time a target cell 42a is recognized, the direction of the liquid flow of the separating liquid inside the sub flow channel 18 is changed. The target cell 42a is led to either of the two branch channels 16a, 16b, and therefore surely collected in the sorting port 30. As a result, target cells 42a can be sorted out at a higher success rate.

By using piezoelectric elements as the liquid flow generating members 22a, 22b, a liquid flow of the separating liquid can be generated with good responsiveness inside the sub flow channel 18. As described above, in the cell sorting device 10, when a target cell 42a is recognized, the drive control member 23 actuates the pair of liquid flow generating members 22 in conjunction with each other.

Figure 7A:
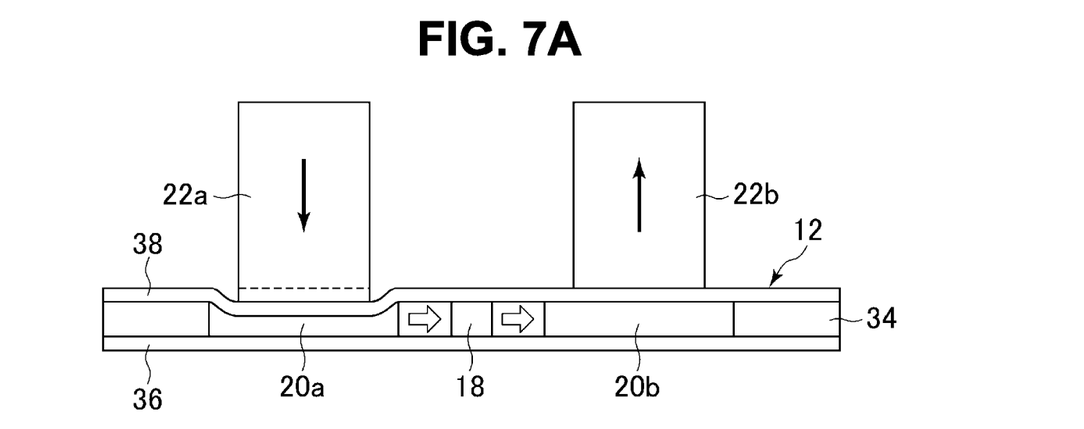
FIG. 7A illustrates a liquid flow in the first direction.

For example, as shown in FIG. 7A, when a voltage is applied to the first liquid flow generating member (piezoelectric element) 22a, a portion of the covering layer 38 over the first liquid reservoir 20a is pushed downward to become into a concave shape. Although not shown in the drawings, a voltage has been applied to the second liquid flow generating member (piezoelectric element) 22b in advance, so that a portion of the covering layer 38 over the second liquid reservoir 20b has been pushed downward to become into a concave shape. In conjunction with the voltage application to the first liquid flow generating member 22a, the voltage application to the second liquid flow generating member 22b is stopped. The concaved portion of the covering layer 38 over the second liquid reservoir 20b is restores its shape due to elasticity.

At this moment, the separating liquid is pushed from the first liquid reservoir 20a into the sub flow channel 18, and a force acts which pulls the separating liquid from the sub flow channel 18 into the second liquid reservoir 20b. Inside the sub flow channel 18, a liquid flow of the separating liquid is generated for about 10 to 500 μs in the first direction from one end to the other end. Since the liquid flow of the separating liquid in the first direction is generated inside the sub flow channel 18, the target cell 42a in the liquid 40 flowing through the main flow channel 14 is pushed out into the second branch channel 16b as shown in FIG. 4.

Since piezoelectric elements are used as the liquid flow generating members 22a, 22b, a liquid flow of the separating liquid can be generated inside the sub flow channel 18 within about 1 μs after the target cell 42a is recognized. The liquid flow of the separating liquid has a flow rate of about 0.01 to 10 m/s.

Figure 7B:
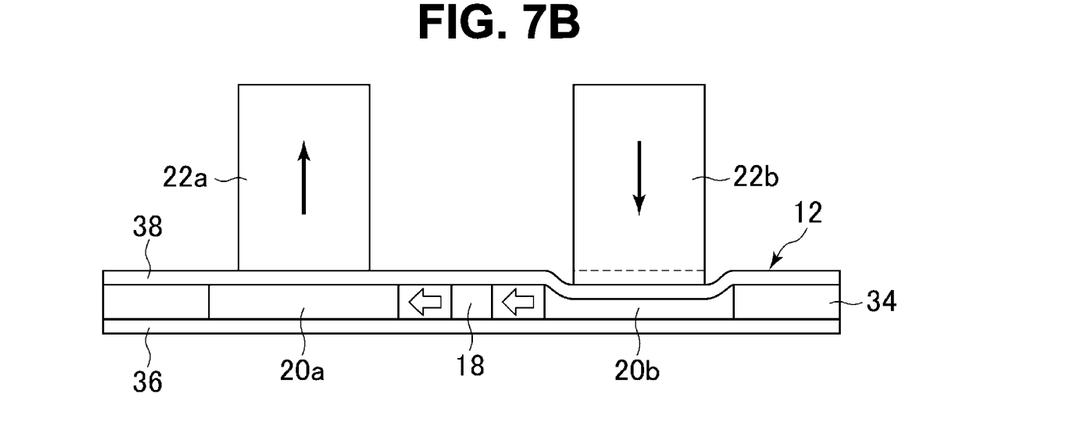
FIG. 7B illustrates a liquid flow in the second direction.

Until a next target cell 42a is recognized, no signal is sent from the drive control member 23 to the liquid flow generating members 22a, 22b, and accordingly the liquid flow generating members 22a, 22b are in a standby state. Subsequently, when a target cell 42a (not shown) is recognized, as shown in FIG. 7B, the voltage application to the first liquid flow generating member 22a is stopped, and in conjunction with this, a voltage is applied to the second liquid flow generating member 22b. The portion of the covering layer 38 over the first liquid reservoir 20a restores its shape due to elasticity, and the portion of the covering layer 38 over the second liquid reservoir 20b is pushed downward to become into a concave shape.

At this moment, the separating liquid is pushed from the second liquid reservoir 20b into the sub flow channel 18, and a force acts which pulls the separating liquid from the sub flow channel 18 into the first liquid reservoir 20a. Inside the sub flow channel 18, a liquid flow of the separating liquid is generated for about 10 to 500 μs in the second direction opposite to the first direction. Since the liquid flow of the separating liquid in the second direction is generated inside the sub flow channel 18, the target cell 42a in the liquid 40 flowing through the main flow channel 14 is pushed out into the first branch channel 16a as shown in FIG. 5.

If a target cell 42a is recognized once more, a liquid flow of the separating liquid is generated in the first direction inside the sub flow channel 18, and the target cell 42a is pushed out into the second branch channel 16b, as described with reference to FIG. 7A.

By providing piezoelectric elements as the liquid flow generating members 22a, 22b on the surface of the substrate 12 above the reservoirs 20a, 20b at opposite ends of the sub flow channel 18, a liquid flow of the separating liquid can be generated with high responsiveness inside the sub flow channel 18.

As described above, in this embodiment, the pair of liquid flow generating members 22 are actuated in conjunction with each other so as to form a liquid flow in the first direction from one end to the other end of the sub flow channel 18 and a liquid flow in the second direction opposite to the first direction, so that target cells 42a can be sorted out at a higher success rate and at a higher speed.

(Modification)

The present invention is not limited to the above described embodiment, which can be appropriately modified within the scope of the spirit of the present invention.

Although borosilicate glass is used as the material of the covering layer 38 in the substrate 12 in the above described embodiment, other materials having elasticity may be used instead. For example, other glass selected from blue plate glass, white plate glass, alkali-free glass, synthetic quartz glass, and alumina borate glass may be used as the material of the covering layer 38. Alternatively, crystal, quartz, silicon, silicon carbide, sapphire, or gallium nitride may be used as the covering layer 38. Further, the covering layer 38 may be formed of piezoelectric material, resin, or metal. Examples of the piezoelectric material may include artificial ceramics such as lead zirconate titanate and lithium niobate. Example of the resin may include polydimethylsiloxane, polymethylmethacrylate resin, polytetrafluoroethylene, polypropylene, and polyvinyl chloride. Examples of the metal may include aluminum, stainless steel, brass, titanium, and other alloys. These materials may be used as the support layer 36.

Although silicon is used as the material of the flow channel layer 34 in the substrate 12, other materials may be used instead as long as patterning of a predetermined flow channel or the like is possible. For example, the material of the flow channel layer 34 may be selected from a glass material such as borosilicate glass, resin materials such as polydimethylsiloxane, polymethylmethacrylate resin, polytetrafluoroethylene, polypropylene and polyvinyl chloride, and a thin film metal material.

The two branch channels 16a, 16b constituting the selection flow channel 16 and provided in the flow channel layer 34 are not necessarily required to join downstream. In this case, target cells 42a can be collected in sorting ports 30 which are provided at respective downstream ends of the first branch channel 16a and the second branch channel 16b.

The width of each flow channel (the main flow channel 14, the sub flow channel 18, the selection flow channel 16), the size and the shape of each inlet (the sample inlet 24, the sheath liquid inlet 26, the buffer solution inlet 28), and the size and the shape of each port (the sorting port 30, the waste port 32) can be appropriately set in consideration of the size and the type of target cells, the whole size of the whole cell sorting device, and so on.

Although piezoelectric actuators are used as the first and second liquid flow generating members 22a, 22b in the above described embodiment, the flow generating members are not limited thereto. Any members that are driven in conjunction with each other to generate a liquid flow in the sub flow channel 18 may be used as the first and second liquid flow generating members 22a, 22b, and provided at opposite ends of the sub flow channel 18. As the liquid flow generating members 22a, 22b, other types of actuators selected from, for example, electromagnetic actuator, electrostatic actuator, thermal actuator, pneumatic actuator, hydraulic actuator, and ultrasonic actuator may be used. Further, syringe pumps may be used as the first and second liquid flow generating members 22a, 22b.

The drive control member 23 for actuating the pair of liquid flow generating members 22 can be appropriately selected depending on the liquid flow generating members 22a, 22b.

Pushing and pulling of the separating liquid are not necessarily required to be completely synchronized, and there may be a difference of about 1 to 100 μs between the timing of respective starts. For example, some liquid flow generating members may perform pulling of the separating liquid before pushing of the separating liquid.

Since the sub flow channel 18 through which the separating liquid flows in two directions is provided so as to intersect with the main flow channel 14, and the pair of liquid flow generating members 22 operating in conjunction with each other are arranged at opposite ends of the sub flow channel 18, the effects of the present invention can be obtained.

REFERENCE SIGNS LIST

10 Cell sorting device
12 Substrate
14 Main flow channel
16a, 16b Branch channel
18 Sub flow channel
22a, 22b Liquid flow generating member
23 Drive control member

The invention claimed is:

1. A cell sorting device comprising:
a substrate comprising an elastic covering layer;
a main flow channel configured so that through which a liquid containing a row of cells including one or more target cells and one or more non-target cells flows, in which a cell separation area for separating the target cells from the row of cells is provided at a halfway position in a flow direction, and through which a liquid containing a row of non-target cells including the non-target cells flows downstream of the cell separation area, the main flow channel being formed in the substrate;
a first selection flow channel and a second selection flow channel configured so that through which a liquid containing a row of target cells including the target cells separated from the main flow channel flows, the first selection flow channel and the second selection flow channel being formed in the substrate so as to branch from the main flow channel onto opposite sides of the main flow channel downstream of the cell separation area;
a sub flow channel configured so that through which a separating liquid flows, the separating liquid provided for separating the target cells from the row of cells and pushing out the target cells into the first selection flow channel or the second selection flow channel, the sub flow channel being formed in the substrate so as to intersect with the main flow channel in the cell separation area;
a first liquid reservoir coupled to a first end of the sub flow channel;
a second liquid reservoir coupled to a second end of the sub flow channel;
a pair of liquid flow generating members, each said liquid flow generating member
disposed on the elastic covering layer of the substrate so as to be respectively located adjacent to and vertically aligned with the first or second liquid reservoir,
configured to cause deformation of the elastic covering layer of the substrate for pushing the separating liquid from the first or second liquid reservoir through the sub flow channel towards the main flow channel, and
configured to allow the elastic covering layer of the substrate to return to an undeformed shape for pulling the separating liquid from the main flow channel through the sub flow channel and into the first or second liquid reservoir; and
a drive control member configured to,
as a first one of the target cells passing through the cell separation area is recognized, actuate the pair of liquid flow generating members in conjunction with each other such that a first one of the pair of liquid flow generating members pushes the separating liquid out of the first liquid reservoir and a second one of the pair of liquid flow generating members pulls the separating liquid into the second liquid reservoir, so that the separating liquid forms a liquid flow in a first direction from the first end to the second end of the sub flow channel, and
as a second one of the target cells passing through the cell separation area next to the first one of the target cells is recognized, actuate the pair of liquid flow generating members in conjunction with each other such that the second one of the pair liquid flow generating members pushes the separating liquid out of the second liquid reservoir and the first one of the pair of liquid flow generating members pulls the separating liquid into the second liquid reservoir, so that the separating liquid forms a liquid flow in a second direction from the second end to the first end of the sub flow channel.

2. The cell sorting device according to claim 1, wherein the drive control member places the liquid flow generating members in a standby state when none of the target cells is recognized.

3. The cell sorting device according to claim 1, wherein the first selection flow channel and the second selection flow channel are provided symmetrically with respect to the main flow channel.

4. The cell sorting device according to claim 1, wherein the first selection flow channel and the second selection flow channel join downstream and are connected to a sorting port for collecting the target cells, and the main flow channel is connected downstream to a waste port for collecting the non-target cells.

5. The cell sorting device according to claim 1, wherein the substrate comprises a flow channel layer having the main flow channel, the first selection flow channel, the second selection flow channel and the sub flow channel, and the elastic covering layer provided so as to cover an upper surface of the flow channel layer.

6. The cell sorting device according to claim 5, wherein each of the pair of liquid flow generating members is a piezoelectric element provided on the elastic covering layer.

7. The cell sorting device according to claim 5, wherein the elastic covering layer is made of borosilicate glass.

8. The cell sorting device according to claim 1, wherein the drive control member actuates the pair of liquid flow generating members so that an amount of the separating liquid that flows into the cell separation area equals to an amount of the separating liquid that flows out from the cell separation area.

9. A cell sorting method that uses the device of claim 1, the method comprising the steps of:
   flowing the liquid containing a row of cells including one or more target cells and one or more non-target cells, through the main flow channel;
   when the first one of the target cells is recognized in the row of cells passing through the cell separation area, actuating the pair of liquid flow generating members in conjunction with each other such that the first one of the pair of liquid flow generating members pushes the separating liquid out of the first liquid reservoir and the second one of the pair of liquid flow generating members pulls the separating liquid into the second liquid reservoir, so that the separating liquid forms the liquid flow in the first direction from the first end to the second end of the sub flow channel, thereby separating the first one of the target cells from the row of cells and pushing the first one of the target cells into the first selection flow channel; and
   when the second one of the target cells passing through the cell separation area next to the first one of the target cells is recognized, actuating the pair of liquid flow generating members in conjunction with each other such that the second one of the pair of liquid flow generating members pushes the separating liquid out of the second liquid reservoir and the first one of the pair of liquid flow generating members pulls the separating liquid into the second liquid reservoir, so that the separating liquid forms the liquid flow in the second direction from the second end to the first end of the sub flow channel, thereby separating the second one of the target cells from the row of cells and pushing the second one of the target cells into the second selection flow channel.

* * * * *